US00PP13112P2

(12) United States Plant Patent
Alderden

(10) Patent No.: US PP13,112 P2
(45) Date of Patent: Oct. 22, 2002

(54) GUZMANIA PLANT NAMED 'PURPLE AND STRIPES'

(76) Inventor: André B. Alderden, Aalsmeerderweg 682, 1435 ER Rijsenhout (NL)

( * ) Notice: Subject to any disclaimer, the term of this patent is extended or adjusted under 35 U.S.C. 154(b) by 0 days.

(21) Appl. No.: 09/888,529

(22) Filed: Jun. 26, 2001

(51) Int. Cl.[7] ..... A01H 5/00
(52) U.S. Cl. ..... Plt./371

(58) Field of Search ..... Plt./371

*Primary Examiner*—Kent L. Bell
(74) *Attorney, Agent, or Firm*—Foley & Lardner

(57) ABSTRACT

A new and distinct cultivar of Guzmania plant named 'Purple and Stripes', as described and illustrated, and particularly characterized by the combined features of: a compound inflorescence, long lasting blooming habit; superior purple primary bract production with RHS color 187D and RHS color 59B variegated leaves, green in the middle and white on the sides.

2 Drawing Sheets

BOTANICAL CLASSIFICATION

*Guzmania lingulata×wittmackii.*

VARIETY DENOMINATION

'Purple and Stripes'.

BACKGROUND OF THE INVENTION

The present invention relates to a new and distinct cultivar of Guzmania plant known by the cultivar name 'Purple and Stripes', and botanically known as Guzmania.

This new Guzmania 'Purple and Stripes' is a branch mutation of hybrid Guzmania 'Luna' of the family Bromeliaceae. The male parent plant of the 'Luna' is a *Guzmania wittmackii* and the female parent plant of the 'Luna' is a *Guzmania lingulata*. Guzmania 'Purple and Stripes' flowered for the first time in 1987 and was discovered in 1987 by the inventor, André B. Alderden, in Rijsenhout, the Netherlands.

Horticultural examination initiated in 1987 and continuing thereafter, has demonstrated that the combination of characteristics as herein disclosed for 'Purple and Stripes' are firmly fixed and are retained through successive generations of asexual reproduction. The new cultivar reproduces true to type.

BRIEF DESCRIPTION OF THE INVENTION

The following traits have been repeatedly observed and are determined to be basic characteristics of 'Purple and Stripes' which in combination distinguish this Guzmania as a new and distinct cultivar:

1. Has a compound inflorescence;
2. Long lasting blooming habit;
3. Superior purple primary bract production with RHS color 187D and RHS color 59B
4. Variegated leaves, green in the middle and white on the sides.

The closest comparison cultivar is Guzmania 'Luna' (unpatented). The most important difference is the color of the leaves. Guzmania 'Purple and Stripes' has variegated leaves (white on the side and green in the middle) and Guzmania 'Luna' does not have variegated leaves.

The new cultivar flowers approximately 17 weeks after treatment with Acetylene.

Guzmania 'Purple and Stripes' is not tested under all available environmental conditions like temperature, light intensity, day length, fertilizers and humidity.

Guzmania 'Purple and Stripes' is a solid, good tenable, long lasting hybrid with a superior margined bract production and a compound purple inflorescence.

BRIEF DESCRIPTION OF THE DRAWING

The accompanying color photographic drawings show a typical inflorescence and foliage of 'Purple and Stripes', with colors being as true as possible with illustrations of this type.

DETAILED BOTANICAL DESCRIPTION

Figure 1:
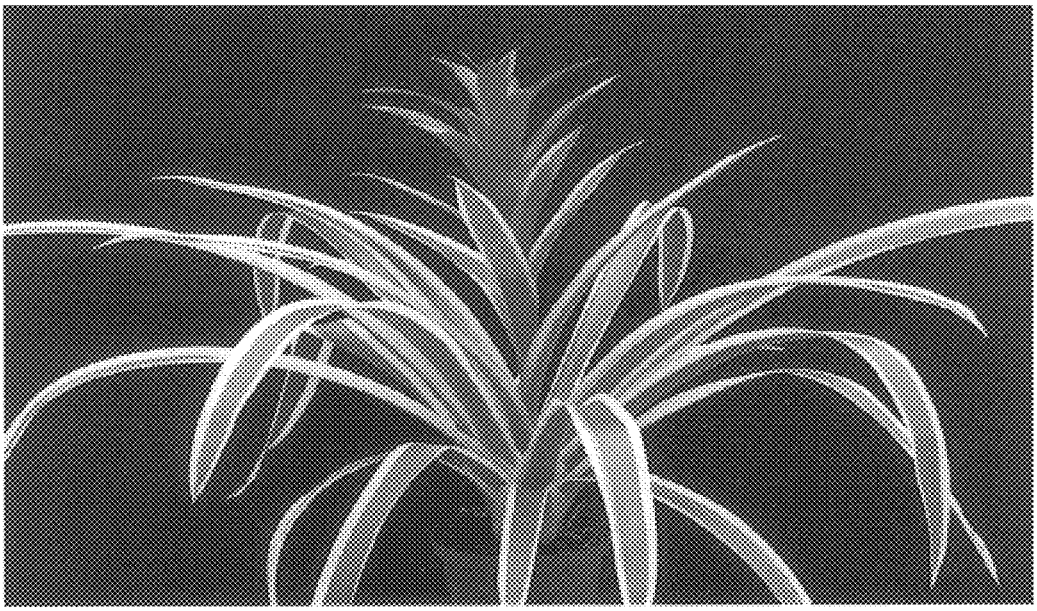
FIG. 1 is a side-view of 'Purple and Stripes' showing a typical inflorescence and foliage.
Figure 2:
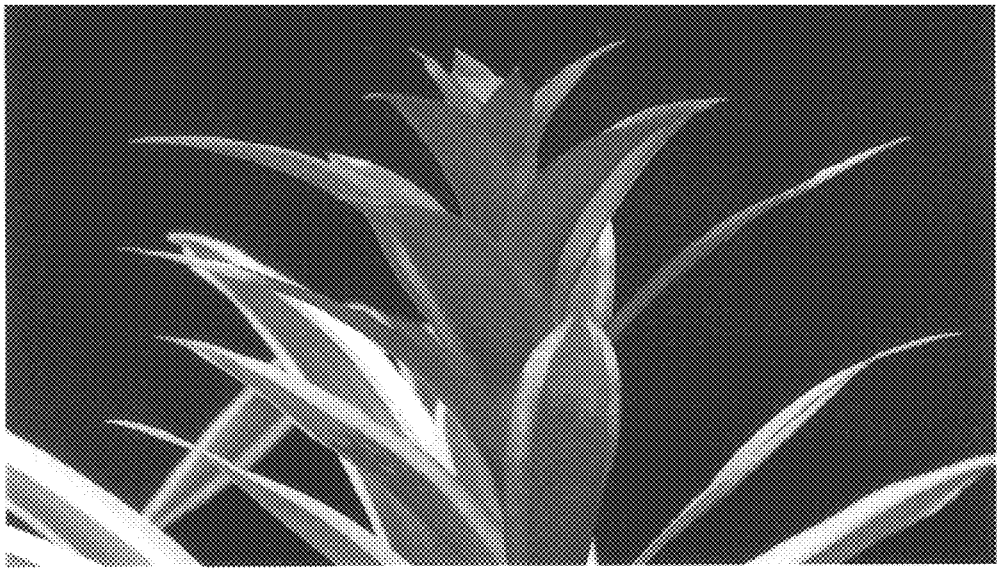
FIG. 2 is a close-up view of an inflorescence and leaves of 'Purple and Stripes'.

Observations, measurements and descriptions of approximately 12 month old plants after potting of Guzmania 'Purple and Stripes' were done under Dutch greenhouse conditions. In the following description, color references are made to The Royal Horticultural Society Colour Chart (R.H.S.), except where colors of ordinary significance are used.

Plant:

*Form.*—Funnel form rosette.
*Height.*—Approximately 50 cm high (flowering).
*Growth habit.*—Stemless.
*Diameter.*—Approximately 80 cm.
*Vigor.*—It takes approximately 12 months after potting to produce a fully grown, finished flowering plant.

Foliage:

*Size of leaf.*—Length approximately 45 cm, width approximately 4–5 cm.
*Shape of leaf.*—(Linear) lanceolate.
*Surface texture.*—Smooth.
*Apex.*—Acute.
*Variegation.*—Marginated.

*Color*.—Upperside middle part RHS 139A, margin color is 158C underside middle part RHS 137B, margin color is 158B.

*Number of leaves*.—Approximately 35.

Bracts:

*Scape bracts*.— Length: The lowest approximately 37 cm, to approximately 20 cm just below the primary bracts. Width: Approximately 3–4 cm. Number: Approximately 8. General Shape: Lanceolate. Texture: Smooth. Margin: Entire. Apex: Acute. Color: 187D Base becoming 139A, middle portion, and 158C, margin, towards apex (Both surfaces).

*Primary bracts*.—Length: The lowest approximately 20 cm, to approximately 8 cm at the top. Width: Approximately 1–3 cm. Number: Approximately 10. Color: Middle part is RHS color 187 D; the margin color is RHS 59 B (Both surfaces). General Shape: Lanceolate. Texture: Smooth. Margin: Entire. Apex: Acute.

*Floral bracts*.—Length: Approximately 2–5 cm. Width: Approximately 1–3 cm. Number: 7. Texture: Smooth. Margin: Entire. Apex: Acute. Color: RHS 155D (Both surfaces).

Flowers:

*Borne:* (*stalks*).—Erect.

*Type of inflorescence*.—Compound.

*Size of inflorescence on stalk*.—Approximately 15 cm in length.

*Diameter of inflorescence*.—Approximately 20 cm.

*Individual petals*.—The individual petals cannot be seen because they are totally hidden within the inflorescence. There are three petals per flower having a length of 5 cm and a width of 0.5 cm. The petals are white RHS 155D (Both surfaces).

Time of blooming: A fully grown plant can produce an inflorescence containing approximately 80 flowers which do not come out and can bloom anytime throughout the year starting approximately 17 weeks after natural induction or induction with acetylene. The inflorescence color lasts approximately 3 months.

Seed characteristics: The plant is a sterile hybrid, therefore no fruit or seed is produced.

Pest/disease resistance/susceptibility: No observations made to date.

I claim:

1. A new and distinct cultivar of Guzmania plant named 'Purple and Stripes', as described and illustrated herein.

* * * * *